US007056711B2

(12) United States Patent
Denholm et al.

(10) Patent No.: US 7,056,711 B2
(45) Date of Patent: Jun. 6, 2006

(54) ATTENUATION OF FIBROBLAST PROLIFERATION

(76) Inventors: Elizabeth M. Denholm, 2 Victoria Avenue, Pointe Claire, Quebec (CA) H9S 4S3; Elizabeth Cauchon, 14750 rue Aurnais, Ste. Genevieve, Quebec (CA) H9H 4Y3; Paul J. Silver, 154 Barton Dr., Spring City, PA (US) 19475-3418

(*) Notice: Subject to any disclaimer, the term of this patent is extended or adjusted under 35 U.S.C. 154(b) by 1010 days.

(21) Appl. No.: 09/727,873

(22) Filed: Dec. 1, 2000

(65) Prior Publication Data

US 2002/0102249 A1    Aug. 1, 2002

Related U.S. Application Data

(60) Provisional application No. 60/168,518, filed on Dec. 2, 1999.

(51) Int. Cl.
*C12N 9/00* (2006.01)

(52) U.S. Cl. .................................................. 435/183
(58) Field of Classification Search ................ 435/232; 424/94.5, 457, 468
See application file for complete search history.

(56) References Cited

U.S. PATENT DOCUMENTS 5,695,752 A    12/1997  Rosen et al.
5,985,582 A *  11/1999  Triscott ...................... 435/7.1
6,153,187 A *  11/2000  Yacoby-Zeevi ............ 424/94.5

FOREIGN PATENT DOCUMENTS

WO    WO 95/13091 A1    5/1995
WO    WO 96/01894 A1    1/1996
WO    WO 98/46258 A2    10/1998
WO    WO 99/484778 A1   9/1999

OTHER PUBLICATIONS

Bensadoun, et al. "Proteoglycan deposition in pulmonary fibrosis," *Amer. J. Respir. Crit. Care Med.* 154:1819-1828 (1996).
Denholm & Phan, "The effects of bleomycin on alveolar macrophage growth factor secretion," *Amer. J. Pathol.* 134:355-363 (1989).
Denholm, "Inhibition of fibroblast by Chondrotinase AC(CAC) and Chondrotinase B(CB)," *FASEB J* 12(5):A948 1998).
Denholm, et al., "Inhibition of human dermal fibroblast proliferation by removal of dermatan sulfate," *European Journal of Pharmacology* 400:145-153 (2000).
Donati, et al., "Treatment of hyertrophic and keloid cicatrices with thiomucase." *Minerva Chirurgica* 30(6):326-33 AN-Medline 76196588 (1975).

Fannon & Nugent, "Basic fibroblast growth factor binds its receptors, is internalized, and stimulates DNA synthesis in Balb/c3T3 cells in the absence of heparan sulfate," *J. Biol. Chem.* 271:17949-17956 (1996).
Forrester, et al., "A paradigm for restenosis based on cell biology: clues for the development of new preventive therapies," *J. Am. Coll. Cardiol.* 17:758-769 (1991).
Jackson, et. al., "Glycosaminoglycans: molecular properties, protein interactions, and role in physiological processes," *Physiol. Rev.* 71:481-530 (1991).
Keller, et al., "Modulation of cell surface heparan sulfate structure by growth of cells in the presence of chlorate," *Biochem.* 28:8100-8107 (1989).
Kjellen & Lindahl, "Proteoglycans: structures and interactions," *Ann. Rev. Biochem.* 60:443-475 (1991).
Linhardt, et al., "Polysaccharide lyases," *Appl. Biochem. Biotech.* 12:135-175 (1986).
Linn, et al. "Isolation and characterization of two chondroitin lyases from Bacteroides thetaiotaomicron," *J. Bacteriol.* 156:859-866 (1983).
Liu & Connolly, "Isolation and characterization of two chondroitin lyases from Bacteroides thetaiotaomicron," *Sem. Cutaneous Med. and Surg.* 17:3-11 (1998).
Lyon, et al., "Hepatocyte growth factor/scatter factor binds with high affinity to dermatan sulfate," *J. Biol. Chem.* 273:271-278 (1998).
Maeda, et al., "6B4 proteoglycan/phosphacan, an extracellular variant of receptor-like protein-tyrosine phosphatase zeta/RPTPbeta, binds pleiotrophin/heparin-binding growth-associated molecule (HB-GAM)," *J. Biol. Chem.* 271:21446-21452 (1996).
Miao, et al., "Heparan sulfate primed on beta-D-xylosides restores binding of basic fibroblast growth factor," *J. Cell. Biochem.* 57:173-184 (1995).
Michelacci, et al., "Isolation and characterization of an induced chondroitinase ABC from Flavobacterium heparinum," *Biochim. Biophys. Acta.* 923:291-201 (1987).
Milev, et al., "The core protein of the chondroitin sulfate proteoglycan phosphacan is a high-affinity ligand of fibroblast growth factor-2 and potentiates its mitogenic activity," *J. Biol. Chem.* 273:21439-21442 (1998).

*Primary Examiner*—Michael Meller
(74) *Attorney, Agent, or Firm*—Pabst Patent Group LLP

(57) ABSTRACT

Highly purified and specific glycosaminoglycan degrading enzymes, chondroitinase B and chondroitinase AC, are used to treat fibroproliferative diseases. The enzymatic removal of chondroitin sulfate B(dermatan sulfate), and to a lesser extent, chondroitin sulfate A or C, from cell surfaces effectively decreases growth factor receptors on the cells and thereby decreases the cell proliferative response to such growth factors. In addition, removal of chondroitin sulfates reduces secretion of collagen, one of the major extracellular matrix components. Through the combined inhibition of fibroblast proliferation and collagen synthesis, treatment with chondroitinase B or chondroitinase AC decreases the size of fibrous tissue found in psoriasis, scleroderma, keloids, pulmonary fibrosis and surgical adhesions.

11 Claims, 6 Drawing Sheets

OTHER PUBLICATIONS

Penc & Gallo, "Dermatan sulfate released after injury is a potent promoter of fibroblast growth factor-2 function," *J. Biol. Chem.* 273:28116-28121 (1998).

Phan & Kunkel, "Lung cytokine production in bleomycin-induced pulmonary fibrosis," *Exper. Lung Res.* 18:29-43 (1992).

Richardson & Hatton, "Transient morphological and biochemical alterations of arterial proteoglycan during early wound healing," *Exp. Mol. Pathol.* 58:77-95 (1993).

Sato, et. al., "Submit structure of Chondroitinase ABC from *Proteus vulgaris,"Agric. Biol. Chem.* 50:1057-1059 (1986).

Schmidt, et al., "The antiproliferative activity of arterial heparan sulfate resides in domains enriched with 2-O-sulfated uronic acid residues," *J. Biol. Chem.* 267:19242-19247 (1992).

Schwartz, "Regulation of chondroitin sulfate synthesis. Effect of beta-xylosides on synthesis of chondroitin sulfate proteoglycan, chondroitin sulfate chains, and core protein," *J. Biol. Chem.* 252:6316-6321 (1977).

Segarini, et al., "Binding of transforming growth factor-beta to cell surface proteins varies with cell type," *Molecular Endocrinol.* 3:261-272 (1989).

Sundberg, et al., "Development and progression of psoriasiform dermatitis and systemic lesions in the flaky skin (fsn) mouse mutant," *Pathobiology* 65:271-286 (1997).

Tabas, et al., "Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation," *J. Biol. Chem.* 268(27):20419-20432 (1993).

Tao, et al., "Elevated expression of proteoglycans in proliferating vascular smooth muscle cells," *Atherosclerosis* 135:171-179 (1997).

Varani, et al., "Expression of serine proteinases and metalloproteinases in organ-cultured human skin. Altered levels in the presence of retinoic acid and possible relationship to retinoid-induced loss of epidermal cohesion," *Amer. J. Pathol.* 145:561-573 (1994).

Vlodavsky, et al., "Control of cell proliferation by heparan sulfate and heparin-binding growth factors," *Thrombosis Haemostasis* 74:534-540 (1995).

Yamagata, et al., "Purification and properties of bacterial chondroitinases and chondrosulfatases," *J. Biol. Chem.* 243:1523-1535 (1968).

Yayon, et al., "Cell surface, heparin-like molecules are required for binding of basic fibroblast growth factor to its high affinity receptor," *Cell* 64:841:848 (1991).

Yeo, et al. Alterations in proteoglycan synthesis common to healing wounds and tumors, *Amer. J. Pathol.* 138:1437-1450 (1991).

Zhang, et al., "In situ hybridization analysis of rat lung alpha 1(I) and alpha 2(I) collagen gene expression in pulmonary fibrosis induced by endotracheal bleomycin injection," *Lab. Invest.* 70: 192-202 (1994).

* cited by examiner

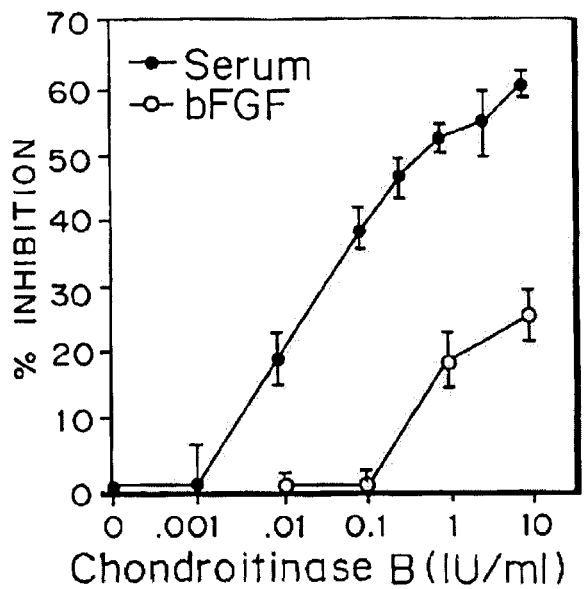
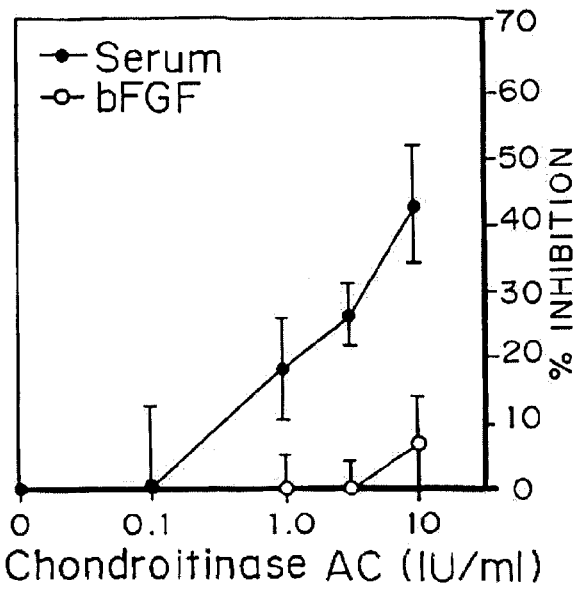
FIG. 5A    FIG. 5B
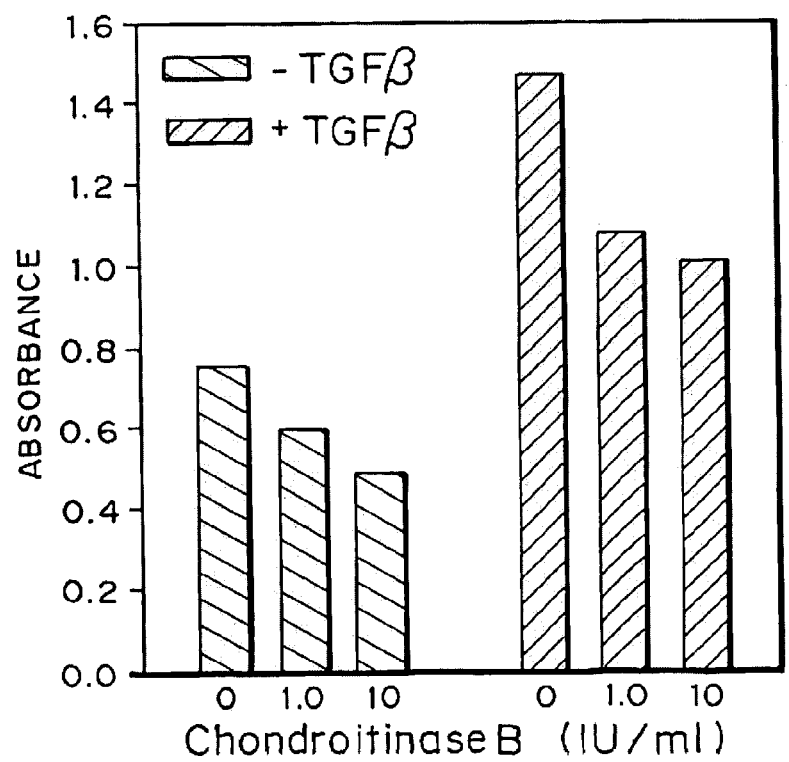
FIG. 6

US 7,056,711 B2

ATTENUATION OF FIBROBLAST PROLIFERATION

This application claims priority to U.S. Ser. No. 60/168,518, filed Dec. 2, 1999.

BACKGROUND OF THE INVENTION

The present invention is a method and composition using chondroitinase B and chondroitinase AC, glycosaminoglycan degrading enzymes, to inhibit the formation of fibrotic tissue.

Proteoglycans on the cell surface and in the extracellular matrix contain variable glycosaminoglycan chains, which include heparan sulfate and chondroitin sulfates A, B, or C. While some proteoglycans contain only one type of glycosaminoglycan, others contain a mixture of heparan and chondroitin sulfates (Jackson et. al., Physiol. Rev. 71:481–530,1991). Extracellular proteoglycans form a structural framework for cells and tissues, and together with cell-associated proteoglycans, have major functions in regulating cell adhesion, migration, and proliferation. The functions of proteoglycans and their component parts have been extensively studied, with much of the emphasis on the roles of heparin and heparan sulfate on cell metabolism (Kjellen, L., and Lindahl, U. (1991) Ann. Rev. Biochem. 60:443–475; Vlodavsky, et al. (1995) Thrombosis Haemostasis 74:534–540; Yayon, et al. (1991) Cell 64:841–848)). Much less is known about the biological activities of proteoglycans containing chondroitin sulfate glycosaminoglycans, and in particular, their effects on cell proliferation.

Two inhibitors of glycosaminoglycan synthesis, chlorate and beta-xyloside, have been used to examine the relative contributions of heparan and chondroitin sulfate proteoglycans to control of the cell cycle (Keller, et al. (1989) Biochem. 28:8100–8107; Miao, et al. (1995) J. Cell. Biochem. 57:713–184; Schwartz, N. B. (1977) J. Biol. Chem. 252:6316–6321). However both of these compounds inhibit the expression of all types of sulfated glycosaminoglycans. There are currently no inhibitors which can selectively block the synthesis or expression of chondroitin sulfate A, B or C. However, specific glycosaminoglycan lyases which can remove either heparan or chondroitin sulfates A, B or C from cells are available. Chondroitinases have been isolated from several bacterial species: *Flavobacterium heparinum, Aeromonas* sp., *Proteus vulgaris, Aurebacterium* sp. and *Bacillus thetaiotamicron* (Linhardt, et al. (1986) Appl. Biochem. Biotech. 12:135–175; Linn, et al. (1983) J. Bacteriol. 156:859–866; Michellacci, et al. (1987) Biochim. Biophys. Acta. 923:291–301; and Sato, et al. (1986) Agric. Biol. Chem. 50:1057–1059).

Most studies examining the activities of chondroitin sulfate proteoglycans (Lyon, et al. (1998) J. Biol. Chem. 273:271–278; Maeda, et al. (1996) J. Biol. Chem. 271:21446–21452; Milev, et al. (1998) J. Biol. Chem. 273:21439–21442; Rapraeger, 1989, and Schmidt, et al. (1992) J. Biol. Chem. 267:19242–19247) have utilized one such enzyme, chondroitinase ABC (from *Proteus vulgaris,* Yamagata, et al. (1968) J. Biol. Chem. 243:1523–1535) which degrades all chondroitin sulfates (chondroitin sulfate A, chondroitin sulfate C and chondroitin sulfate B). Since chondroitinase ABC acts on more than one type of chondroitin sulfate, it is not possible to determine the biological activity of the individual types of chondroitin sulfates using this enzyme.

Evidence for a role of chondroitin sulfate A or B or C proteoglycans in cell proliferation includes data which shows upregulation during rapid cell proliferation, as occurs in wound healing (Penc and Gallo (1998) J. Biol. Chem. 273:28116–28121; Yeo, et al. (1991) Amer. J. Pathol. 138:1437–1450) and down regulation in quiescent cells (Tao et. al. (1997) Atherosclerosis 135:171–179). Such studies suggest that there may be a relationship between the secretion and expression of cell surface chondroitin sulfate proteoglycans and cell proliferation.

Recent studies in wound healing have found that chondroitin sulfate B proteoglycans are present in high concentration in the fluid of healing wounds, and that addition of these proteoglycans to a wounded area may promote healing (Penc and Gallo, 1998). Although the mechanism of action of the chondroitin sulfate B in wound healing is unknown, it is possible that these proteoglycans may directly or indirectly affect cell proliferation.

It is therefore an object of the present invention to provide a method and compositions for treatment of conditions associated with abnormal formation of fibrous tissue, through modification of proteoglycans.

It is another object of the present invention to provide a method and compositions to modulate collagen synthesis, decrease TGFbeta production, decrease fibroblast proliferation or migration, release chondroitin sulfate proteoglycans from cells, and decrease growth factor binding sites on fibroblasts.

It is a further object of the present invention to provide a method and compositions to treat disorders which involve hyperproliferation of fibroblasts such as scleroderma, psoriasis, keloids, pulmonary fibrosis and surgical adhesions.

SUMMARY OF THE INVENTION

Highly purified and specific glycosaminoglycan degrading enzymes, chondroitinase B and chondroitinase AC, are used to treat fibroproliferative diseases. The enzymatic removal of chondroitin sulfate B, and to a lesser extent, chondroitin sulfate A or C, from cell surfaces effectively decreases growth factor receptors on the cells and thereby decreases the cell proliferative response to such growth factors. In addition, removal of chondroitin sulfates reduces secretion of collagen, one of the major extracellular matrix components. Through the combined inhibition of fibroblast proliferation and collagen synthesis, treatment with chondroitinase B or chondroitinase AC decreases the size of fibrous tissue found in psoriasis, scleroderma, keloids and surgical adhesions.

BRIEF DESCRIPTION OF THE DRAWINGS

FIG. 1A shows the release of $^{35}$S-glycosaminoglycans after treatment with 1.0 IU/ml of enzyme for the indicated time (min). FIG. 1B shows the release of $^{35}$S-glycosaminoglycans after treatment with the indicated concentration of enzyme for one hr. Data are the cpm/well of $^{35}$S-glycosaminoglycans released by enzyme treatment (cpm enzyme treated cells minus cpm cells treated with medium alone), from a representative of two such experiments performed in triplicate. Mean cpm released by medium alone was 8,160±599.

FIGS. 5A and 5B are graphs of the dose dependent effects of *Flavobacterium heparinum* derived chondroitinase B (FIG. 5A) and chondroitinase AC (FIG. 5B) on fibroblast proliferation in response to 10% fetal bovine serum (serum) (●) or 100 pg/ml bFGF (○). Data are the % inhibition of proliferation for cells treated with chondroitinase B compared to cells treated with medium alone. Each point is the mean±sem of four experiments performed in triplicate.

FIG. 6 is a graph of the collagen content of the extracellular matrix of fibroblasts treated with 0 to 10 IU/ml of *Flavobacterium heparinum* derived chondroitinase B, in the absence (cross hatched) or presence (black) of 25 ng/ml TGF-beta.

DETAILED DESCRIPTION OF THE INVENTION

Figure 1A:
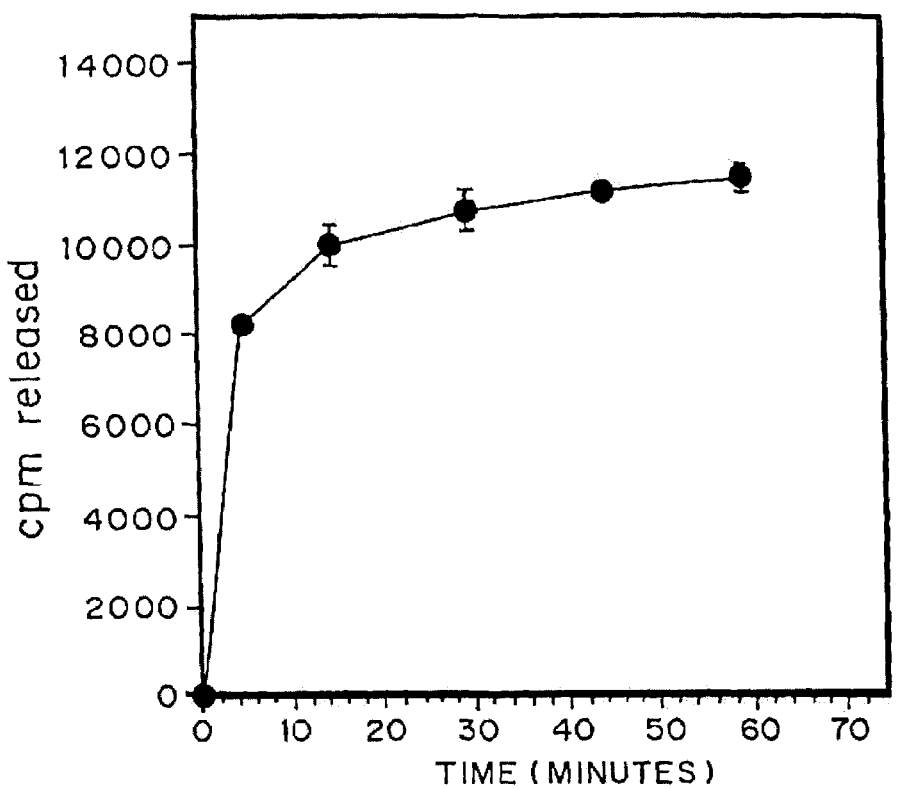
FIGS. 1A and 1B are graphs of the release of sulfated glycosaminoglycan from fibroblasts, following treatment with *Flavobacterium heparinum* derived Chondroitinase B, as a function of time (FIG. 1A) or dose (FIG. 1B).

Glycosaminoglycans, including chondroitin sulfates A, B or C, and heparan sulfate, are the sulfated polysaccharide components of proteoglycans located on cell surfaces, where they act as co-receptors for cytokines and growth factors and in the extracellular space where they form the structure of the extracellular matrix and serve as a supporting and organizational structure of tissues and organs.

Two ultra-purified enzymes from *Flavobacterium heparinum*, chondroitinase B whose sole substrate is chondroitin sulfate B, and chondroitinase AC whose substrates are chondroitin sulfate A and C, have made it possible to distinguish between the activities of the different chondroitin sulfates and to directly assess their influence on human skin fibroblast proliferation. Starting from the premise that chondroitin sulfate proteoglycans promote cell proliferation, it has now been demonstrated that removal of chondroitin sulfate B, and, to a lesser extent, chondroitin sulfate A or C, inhibits cell proliferation.

The method for inhibiting events in the fibrotic process by the use of a highly purified glycosaminoglycan degrading enzyme, preferably from *Flavobacterium heparinum*, is demonstrated in the examples.

Enzyme Formulations
Enzymes

The chondroitinase B and chondroitinase AC described in the examples are glycosaminoglycan degrading enzymes from *Flavobacterium heparinum*. Both enzymes modulate the interactions involved in cell proliferation and extracellular matrix synthesis by i) releasing chondroitin sulfate proteoglycans from cells; ii) decreasing growth factor binding sites on cells; iii) decreasing fibroblast proliferation; iv) decreasing TGFbeta production, and v) decreasing collagen synthesis and thereby decreasing fibrous tissue formation.

Glycosaminoglycans are unbranched polysaccharides consisting of alternating hexosamine and hexuronic residues which carry sulfate groups in different positions. This class of molecules can be divided into three families according to the composition of the disaccharide backbone. These are: heparin/heparan sulfate [HexA-GlcNAc(SO$_4$)]; chondroitin sulfate [HexA-GalNAc]; and keratan sulfate [Gal-GlcNAc].

Representative glycosaminoglycan degrading enzymes include heparinase 1 from *Flavobacterium heparinum*, heparinase 2 from *Flavobacterium heparinum*, heparinase 3 from *Flavobacterium heparinum*, chondroitinase AC from *Flavobacterium heparinum*, and chondroitinase B from *Flavobacterium heparinum*, heparinase from *Bacteroides* strains, heparinase from *Flavobacterium* Hp206, heparinase from *Cytophagia* species, chondroitin sulfate degrading enzymes from *Bacteroides* species, chondroitin sulfate degrading enzymes from *Proteus vulgaris*, chondroitin sulfate degrading enzymes from *Microcossus*, chondroitin sulfate degrading enzymes from *Vibrio* species, chondroitin sulfate degrading enzymes from *Arthrobacter aurescens*, these enzymes expressed from recombinant nucleotide sequences in bacteria and combinations thereof. Other enzymes which degrade glycosaminoglycans are present in mammalian cells and include heparanases, arylsulfatase B, N-acetylgalactosamine-6-sulfatase, and iduronate sulfatase.

The chondroitin sulfate family includes seven sub-types designated unsulfated chondroitin sulfate, oversulfated chondroitin sulfate and chondroitin sulfates A–E which vary in the number and position of their sulfate functional groups. Additionally, chondroitin sulfate B, also referred to as dermatan sulfate, differs in that iduronic acid is the predominant residue in the alternative hexuronic acid position.

Chondroitin sulfates A, B and C are the predominant forms found in mammals and may be involved in the modulation of various biological activities including cell differentiation, adhesion, enzymatic pathways and hormone interactions. The presence of chondroitin sulfate proteoglycans is elevated in the later stages of cell growth in response to tissue and vessel damage, as reported by Yeo, et al., *Am. J. Pathol.* 138:1437–1450, 1991, Richardson and Hatton, *Exp. Mol. Pathol.* 58:77–95, 1993 and Forrester, et al., *J. Am. Coll. Cardiol.* 17:758–769, 1991. Chondroitin sulfates also have been associated with events involved in the progression of vascular disease and lipoprotein uptake as described by Tabas, et al., *J. Biol. Chem.,* 268(27): 20419–20432, 1993.

Chondroitinases have been isolated from several bacterial species: *Flavobacterium heparinum, Aeromonas* sp., *Proteus vulgaris, Aurebacterium* sp. and *Bacillus thetaiotamicron* (Linhardt et. al., 1986; Linn et. al., J. Bacteriol. 156:859–866, 1983; Michelacci et. al., Biochim. Biophys. Acta. 923:291–201, 1987; and Sato et. al., Agric. Biol. Chem. 50:1057–1059, 1986). PCT/US95/08560 "Chondroitin Lyase Enzymes" by Ibex Technologies R and D, Inc., et al. describes methods for purification of naturally produced chondroitinases, especially separation of chondroitinase AC from chondroitinase B, as well as expression and purification of recombinant chondroitinases. Mammalian enzymes which degrade chondroitin sulfates include arylsulfatase B, N-acetylgalactosamine-6-sulfatase, and iduronate sulfatase.

Those enzymes useful in the methods and compositions described herein will cleave proteoglycans on the surfaces of cells, in particular fibroblasts, most preferably those which serve as receptors involved in cell proliferation and/or migration and/or gene expression, particularly of collagen.

Formulations

For topical application, the glycosaminoglycan degrading enzyme is combined with a carrier so that an effective dosage is delivered, based on the desired activity, at the site of application. For topical application, several ointments and cremes are currently used for other therapeutics agents; any one of which can be used for the application of chondroitinase B or AC. The topical composition can be applied to the skin for treatment of diseases such as psoriasis. The carrier may be in the form of an ointment, cream, gel, paste, foam, aerosol, suppository, pad or gelled stick. For topical application, several ointments and cremes are currently used for other therapeutics agents; any one of which can be used for the application of chondroitinase B or AC. A topical composition consists of an effective amount of glycosaminoglycan degrading enzyme in a pharmaceutically acceptable excipient such as buffered saline, mineral oil, vegetable oils such as corn or arachis oil, petroleum jelly, Miglyol 182, alcohol solutions, or liposomes or liposome-like products.

Compositions for local or systemic administration will generally include an inert diluent. For example, for injection, chondroitinase B or AC can be prepared in physiological balanced buffer solutions. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

For directed internal topical applications, the composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. Any of these formulations may also include preservatives, antioxidants, antibiotics, immunosuppressants, and other biologically or pharmaceutically effective agents which do not exert a detrimental effect on the glycosaminoglycan degrading enzyme or cells.

The glycosaminoglycan degrading enzyme can also be administered in combination with a biocompatible polymeric implant which releases the glycosaminoglycan degrading enzyme over a controlled period of time at a selected site. Examples of preferred biodegradable polymeric materials include polyanhydrides, polyorthoesters, polyglycolic acid, polyesters such as polylactic acid, polyglycolic acid, polyethylene vinyl acetate, and copolymers and blends thereof. Examples of preferred non-biodegradable polymeric materials include ethylene vinyl acetate copolymers.

Other Therapeutic Agents which can be Administered in Combination

The glycosaminoglycan degrading enzymes can be administered alone or in combination with other treatments. For example, the enzymes can be administered with antibiotics, antibodies to cytokines and chemokines (such as TNFalpha, TGFbeta, Il-1, Il-6), and anti-inflammatories such as cortisone.

Other combinations will be apparent to those skilled in the art.

Methods of Treatment

Excessive cell proliferation is characteristic of chronic diseases such as psoriasis, scleroderma and pulmonary fibrosis. Each of these diseases represents a complex interaction of the individual cell types composing the involved organ. In general terms these diseases are characterized by uncontrolled cell proliferation and the deposition of excess collagen and glycosaminoglycans (Liu and Connolly (1998) Sem. Cutaneous Med. and Surg. 17:3–11; and Phan, S. H. Fibrotic mechanisms in lung disease. In: Immunology of Inflammation, edited by P. A. Ward, New York: Elsevier, 1983, pp121–162). Although collagen is considered to be the major component of fibrotic scar tissue, recent work has indicated that sulfated glycosaminoglycans may be crucial to the process of collagen deposition and tissue remodeling which occurs in such diseases (Bensadoun, et al. (1996) Amer. J. Respir. Crit. Care Med. 154:1819–1828). A key cell in all these diseases is the fibroblast. Fibroblast proliferation and matrix secretion are responsible for much of the increase in tissue thickness and density. Fibroblasts make a major contribution to the excessive scar tissue in post-surgical adhesions, and in keloids which form after injuries such as burns. The mechanisms controlling fibroblast proliferation and secretion of collagen and glycosaminoglycans are complex substances which activate fibroblasts include cytokines, chemokines and growth factors, produced by other cells, and by fibroblasts themselves. One such cytokine is TGF-beta, considered to be a key controller of collagen synthesis. TGF-beta is secreted by fibroblasts and can feedback to enhance its own secretion, increasing both fibroblast matrix production and proliferation. TGF-beta activities are mediated through the interaction of specific receptors, sulfated glycosaminoglycans associated with them, and with other matrix proteins (Segarini, et al. (1989) Molecular Endocrinol. 3:261–272).

As demonstrated by the examples, the glycosaminoglycan degrading enzyme is administered to the site to be treated in a dosage effective to modulate collagen synthesis, fibroblast proliferation or migration, release chondroitin sulfate proteoglycans from cells; decrease growth factor binding sites on cells, and thereby decrease fibrous tissue formation, as appropriate for the specific application. Application is either topical, localized, sub-dermal or systemic.

Chondroitinase B or chondroitinase AC can be applied topically, for example, to lesions of scleroderma, psoriasis and keloids; or injected sub-dermally (locally), for example, into keloids and surgical adhesions. These chondroitinases may also be used systemically to treat pulmonary fibrosis, either via intravenous injection or via aerosol administration directly into the lungs.

EXAMPLES

The present invention will be further understood by reference to the following non-limiting examples.

Example 1

Enzyme Substrate Specificity

Chondroitinase B (no EC number) and chondroitinase AC (EC 4.2.2.5) are recombinant proteins expressed in *Flavobacterium heparinum* (PCT/US95/08560 "Chondroitin Lyase Enzymes"). Specific activity and substrate specificity were determined for each enzyme, using a kinetic spectrophotometric assay, performed essentially as described in PCT/US95/0856. In these assays, enzyme concentrations were 0.25 IU/ml and substrate concentrations were 0.5 mg/ml (chondroitin sulfate B and chondroitin sulfate AC) or 0.75 mg/ml (heparan sulfate). The specific activities of the enzymes were: 97 IU/mg for Chondroitinase B and 221 IU/mg for chondroitinase AC.

The substrate specificity of ultra-purified Chondroitinase B and AC were determined by testing the ability of the enzymes to degrade chondroitin sulfate B, chondroitin sulfate A, chondroitin sulfate C, and heparan sulfate. As shown in Table 1, both enzymes were active towards the corresponding sulfated glycosaminoglycan, with 0.2% or less activity against any of the other glycosaminoglycans. These results confirm the substrate specificity of the purified Chondroitinase B and Chondroitinase AC used in this application.

TABLE 1

| Comparative Enzymatic Activities Against Glycosaminoglycans | | | | |
|---|---|---|---|---|
| | Substrate | | | |
| Enzyme | CSB | CSA | CSC | HS |
| Chondroitinase B | | | | |
| IU/ml | 399 | 0.04 | 0.03 | 0.92 |
| (relative activity) | (100) | (0.01) | (0.01) | (0.23) |

TABLE 1-continued

| Comparative Enzymatic Activities Against Glycosaminoglycans | | | | |
|---|---|---|---|---|
| | Substrate | | | |
| Enzyme | CSB | CSA | CSC | HS |
| Chondroitinase AC | | | | |
| IU/ml | 0.604 | 1238 | 735 | 2.2 |
| (relative activity) | (0.05) | (100) | (59) | (0.18) |

Enzyme activities are shown as IU/ml with each substrate, and as the relative activity towards each substrate. Relative activity was determined after assigning 100% for the preferred substrate (CSB for chondroitinase B, CSA for chondroitinase AC. CSB=chondroitin sulfate B; CSA=chondroitin sulfate A; CSC=chondroitin sulfate C; HS=heparan sulfate. Substrate concentrations were 500 mcg/ml (CSB, CSA, CSC) or 750 mcg/ml (HS).

Example 2

Removal of Glycosaminoglycans from Cells

The effectiveness of the chondroitinases B and AC in removing sulfated glycosaminoglycans from cells was examined using cells with glycosaminoglycans labeled by incubation with $^{35}$S. Fibroblasts were plated at a density of $6 \times 10^4$ cells/well in 24 well plates, in DMEM with 10% serum. After 24 hrs, medium was changed to Fisher's medium containing 10% serum and 25 microCi/ml of $Na_2^{35}SO_4$, and incubation continued for 2.5 days. The medium was removed and cells rinsed 2× with DMEM then treated with Chondroitinase B or AC as indicated. Medium was removed and radioactivity determined. The release of sulfated glycosaminoglycans from cells by enzyme was expressed as cpm/well of chondroitinase-treated cells minus cpm/well of untreated cells.

Figure 1B:
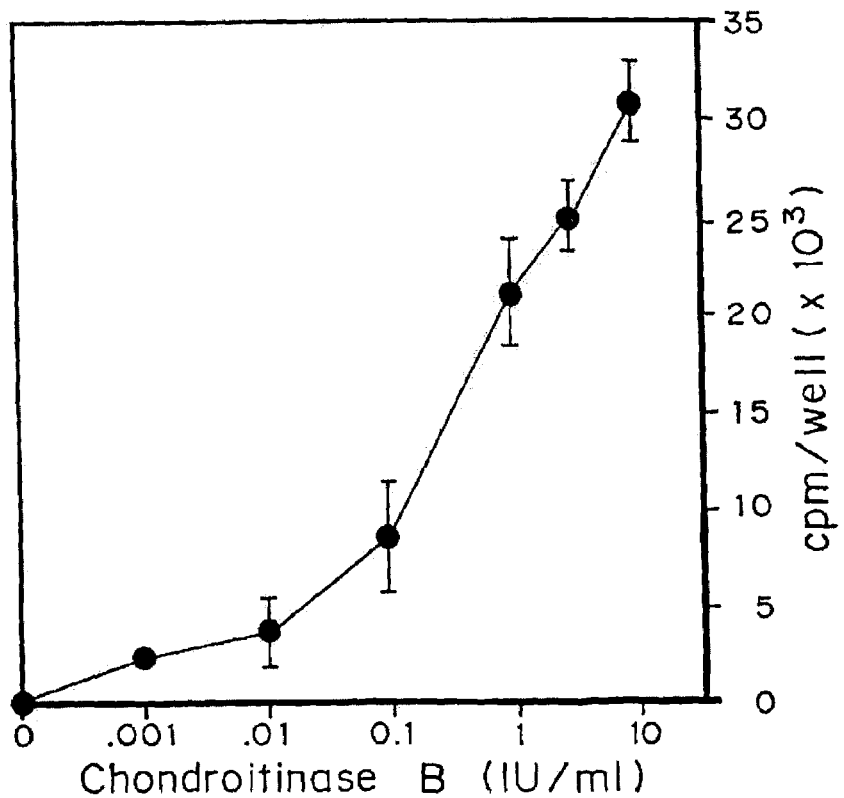

Cells were exposed to 1.0 IU/ml of Chondroitinase B, at 37° C. for variable lengths of time. As shown in FIG. 1A, maximal release of sulfated GAGs by chondroitinase B was achieved following an 1 hour exposure to enzyme. Further experiments were done, in which fibroblasts were treated for 1 hour with varying concentrations of Chondroitinase B. FIG. 1B illustrates that the release of sulfated glycosaminoglycans from fibroblasts was also dependent on the concentration of chondroitinase B used.

Figure 2:
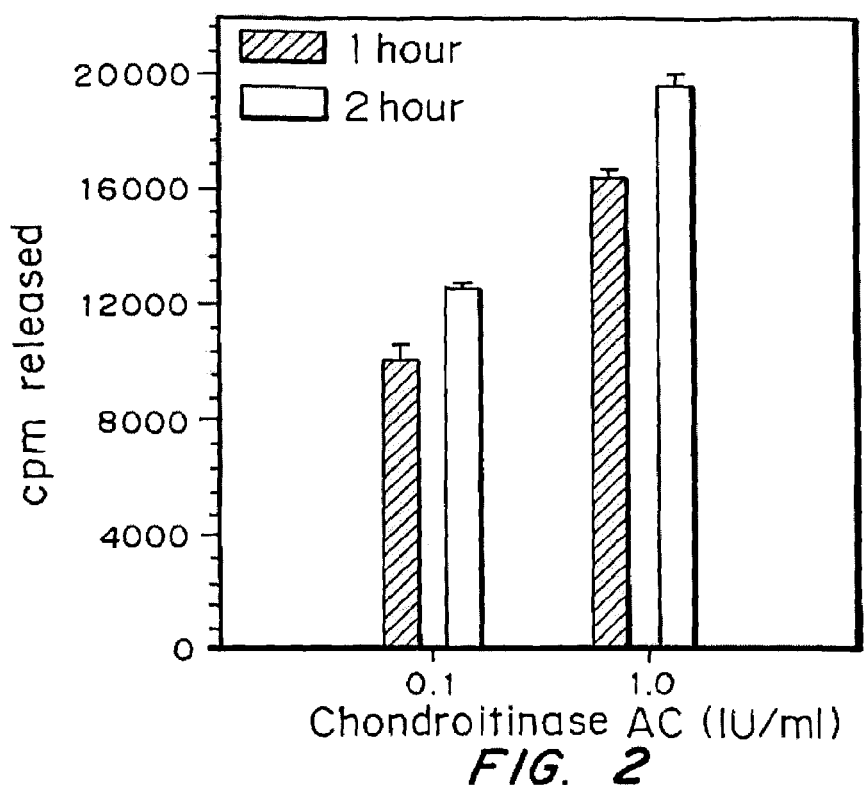
FIG. 2 is a graph of the time and dose dependent release of sulfated glycosaminoglycans from fibroblasts following treatment with *Flavobacterium heparinum* derived Chondroitinase AC. Solid bars represent release after a one hr treatment, and open bars are release after a 2 hr treatment. Data are the cpm/well of $^{35}$S-glycosaminoglycans released by enzyme treatment (cpm enzyme treated cells minus cpm cells treated with medium alone), from a representative of two such experiments performed in triplicate. Mean cpm released by medium alone was 4,028±54.

The release of sulfated GAGs by chondroitinase AC was examined by treating fibroblasts for 1 or 2 hrs with 0.1 and 1.0 IU/ml of enzyme. As shown in FIG. 2, the release of sulfated GAGs by chondroitinase AC was both time and dose dependent. Maximal release was achieved after a 2 hr treatment with 1.0 IU/ml of enzyme.

Example 3

Effects on bFGF Binding

Iodinated bFGF was obtained from Dupont NEN, specific activity greater than 1200 Ci/mmol. Fibroblasts were plated in 48 well dishes and grown to confluence. Prior to binding assays, cells were treated with medium or enzyme as indicated for proliferation assays. Following enzyme treatments, cells were chilled and binding assays carried out at 4° C. Cells were incubated for one hour with 25 ng/ml of $^{125}$I-bFGF alone, or with the addition of 25 microg/ml of unlabelled bFGF in binding buffer (DMEM, 25 mM HEPES, 0.05% gelatin). Following incubation with bFGF, cells were washed 2× with ice cold binding buffer. Glycosaminoglycan-bound $^{125}$I-bFGF was removed with two rinses with wash buffer (2M NaCl in 20 mM HEPES, pH 7.4). Receptor bound $^{125}$I-bFGF was removed by washing 2× with wash buffer (pH 4.0) (Fannon and Nugent (1996) J. Biol. Chem. 271:17949–17956).

Figure 3A:
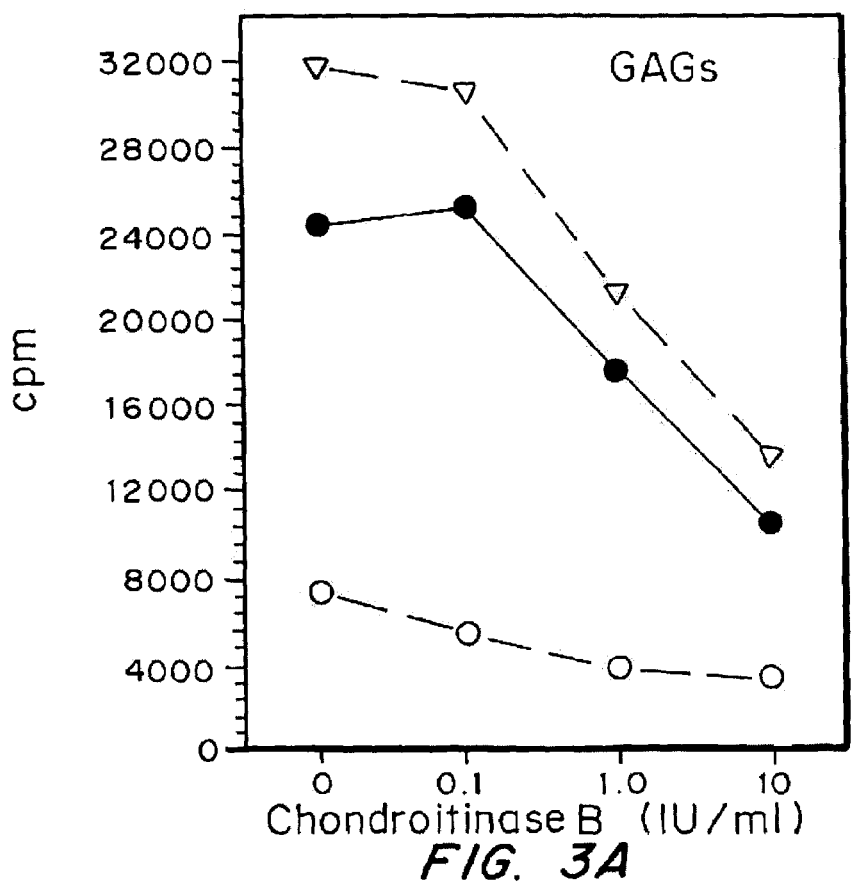
FIGS. 3A and 3B are graphs of the binding of $^{125}$1-bFGF to fibroblast glycosaminoglycans (GAGs, FIG. 3A) and bFGF receptors (FIG. 3B) following treatment with *Flavobacterium heparinum* derived Chondroitinase B. Total (triangles), nonspecific (○) and specific (●) binding are shown. Data is from a representative of five such experiments performed in duplicate.
Figure 3B:
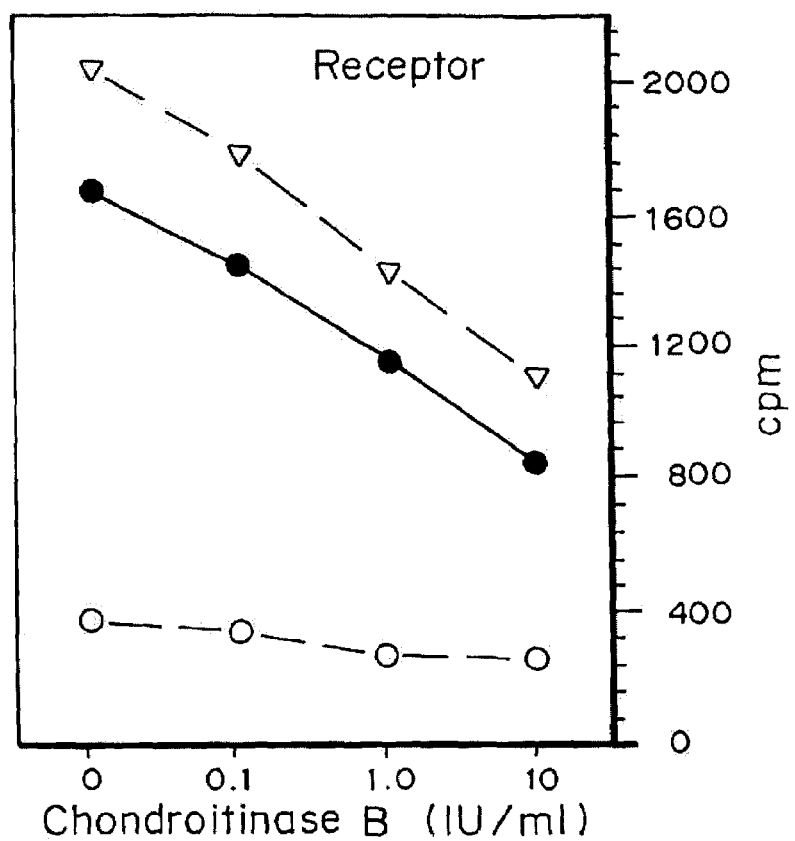

Numerous growth factors have been shown to bind to heparan sulfate proteoglycans on the cell surface. There is however little information on growth factor binding to chondroitin sulfate proteoglycans. The effects of chondroitinase B and chondroitinase AC on the binding of one such growth factor (bFGF), to fibroblasts was therefore examined. On chondroitinase B-treated cells, the amount of bFGF bound to both cell surface glycosaminoglycans and receptors decreased as the concentration of enzyme increased (FIG. 3). Specific binding to glycosaminoglycans was significantly decreased by 51±6% (n=3), at the highest concentration of enzyme used (10 IU/ml). Receptor binding was significantly decreased by 32±9% and 31±8% (n=3) at 1.0 and 10 IU/ml respectively.

Figure 4:
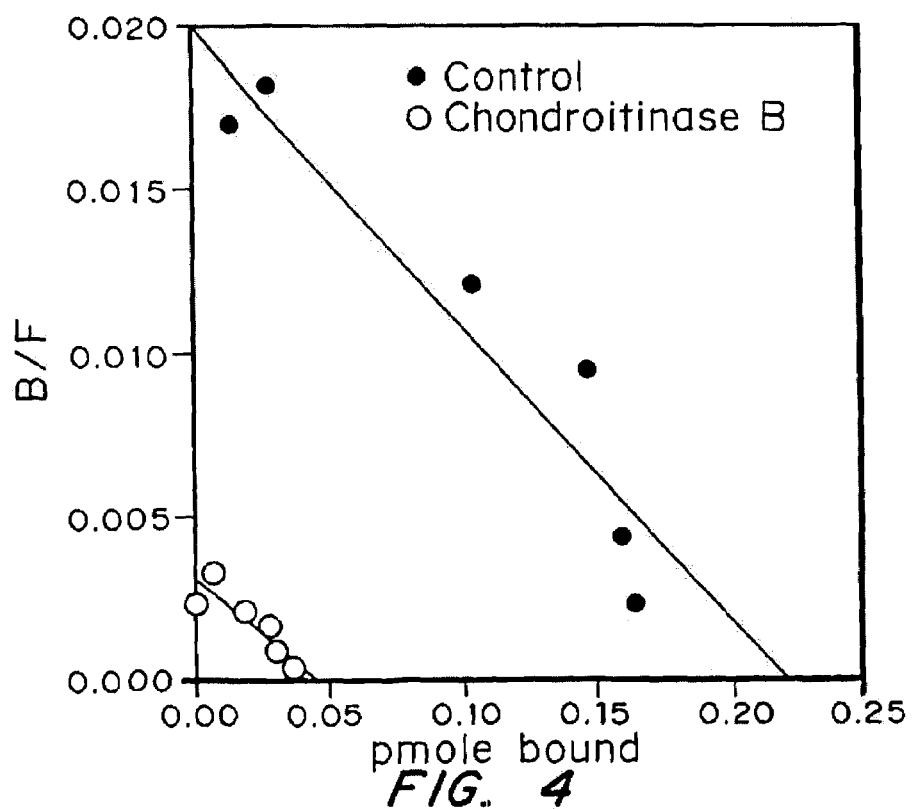
FIG. 4 is a graph of the Scatchard analysis of bFGF bound to receptors of fibroblasts treated with medium (control, ●) or 1.0 IU/ml of *Flavobacterium heparinum* derived chondroitinase B (○). Data are from a representative of five such experiments performed in duplicate.

Scatchard plot analysis of bFGF binding data found a decrease in the number of receptors on chondroitinase B-treated cells when compared to controls, with no change in binding affinity (FIG. 4). Chondroitinase B-treated fibroblasts had 1.8 (±0.6)×10$^5$ receptors while untreated fibroblasts had 3.0 (±0.8)×10$^5$ receptors. The binding affinity in chondroitinase-treated fibroblasts was 15.3±3.6 nM, compared to 16.7±2.9 nM in controls, (n=5).

Chondroitinase AC was less effective in inhibiting bFGF binding to fibroblasts. Binding of bFGF was unaffected by 0.01 to 1.0 IU/ml of chondroitinase AC, though significant inhibition was found with 10 IU/ml. At 10 IU/ml of chondroitinase AC, specific binding to GAGs and receptors was inhibited by 46±2%, and 54±3%, respectively.

Example 4

Effects on Proliferation

Human dermal fibroblasts were obtained from Clonetics, Inc., San Diego, Calif. Cells were cultured in DMEM containing 1% antibiotics and 10% serum. The proliferation assay was performed as previously described (Denholm and Phan (1989) Amer. J. Pathol., 134:355–363). Briefly, cells were plated in DMEM w/10% serum; 24 hrs later medium was replaced with serum free medium, and incubation continued for an additional 24 hrs. Cells were then treated with either serum free DMEM alone, or DMEM containing the indicated concentration of enzyme for 1 hour at 37° C. Following enzyme treatment, cells were rinsed 1× with DMEM, then given DMEM w/10% serum and incubated for 48 hrs. In experiments using bFGF, DMEM containing 2 mg/ml BSA was used, with or without 100 pg/ml bFGF. Controls for each experiment were: (negative) untreated cells incubated in serum free medium, and (positive) untreated cells incubated in DMEM w/10% serum. The number of cells per well was quantitated using the CyQuant assay method from Molecular Probes, Eugene, Oreg. Fluorescence/well was determined using a CytoFluor Series 4000 fluorescent plate reader (PerSeptive Biosystems) and cell numbers calculated from a standard curve. The average number of cells/well in negative controls was 3.0±0.3×10$^4$, and for positive controls was 9.0±0.8×10$^4$ (mean±sem; n=10). Based on controls for each experiment, data is represented as % Inhibition, where: % Inhibition=1−[#cells/well enzyme-treated)/(#cells/well untreated)]×100%.

Experiments were performed to determine if treatment of fibroblasts with chondroitinase B or chondroitinase AC would have an effect on proliferation of these cells. Proliferation of fibroblasts in response to 10% fetal bovine serum (serum) was inhibited in a dose dependent manner when cells were pretreated for 1 hour with 0.01 to 10 IU/ml of Chondroitinase B (FIG. 5A, closed circles). Maximal inhibition of proliferation with chondroitinase B treated fibroblasts was 47 to 63% at 0.3 to 10 IU/ml. Chondroitinase AC treatment of fibroblasts also inhibited the proliferative response to serum in a dose dependent manner (FIG. 5B, closed circles). Inhibition of 19 to 44% was found at doses of 1.0 to 10 IU/ml of chondroitinase AC.

Since binding experiments had revealed that treatment with chondroitinase B and chondroitinase AC had decreased bFGF binding to fibroblasts, the fibroblast proliferation experiments were repeated using bFGF in place of serum. Removal of chondroitin sulfate B with chondroitinase B inhibited the proliferative response to bFGF, in a dose dependent manner (FIG. 5A, open circles). Inhibition of proliferation in response to bFGF, however, required higher concentrations of enzyme than were needed to inhibit the response to serum. No inhibition was observed at chondroitinase B concentrations below 1.0 IU/ml; maximal inhibition was 26±4% at a concentration of 10 IU/ml. There was a significant correlation between the effects of chondroitinase B on bFGF binding to its receptor and the effects on cell proliferation ($r^2$=0.987, p<0.003).

Chondroitinase AC treatment of fibroblasts had little effect on the proliferation of fibroblasts in response to bFGF (FIG. 5B, open circles). As with bFGF binding, 10 IU/ml of chondroitinase AC was required to detect inhibition of proliferation.

Example 5

Inhibition of Collagen Synthesis in Fibroblasts

The effects of Chondroitinase B on the synthesis and secretion of collagen were examined in an ELISA assay. Human dermal fibroblasts were plated into 96 well plates at a density of 1×10$^4$ cells/well, in medium with 10% serum. Three days later, medium was changed to serum-free medium containing 50 µg/ml of ascorbic acid, and incubation continued for 24 more hours. Cells were treated for 1 hour with 0 to 10 IU/ml of Chondroitinase B, then washed 1× with serum-free medium, and given fresh medium with ascorbic acid with or without 25 ng/ml TGF-beta. Fibroblasts were then incubated 72 hours at 37° C. Medium was removed from cells, and cells were lysed by adding a solution of 0.02M NH$_4$OH and 0.5% Triton in phosphate buffered saline (PBS) for 5 mins. The remaining extracellular matrix was washed 2× with PBS. Collagen content of the extracellular matrix was assayed using a direct ELISA, using monoclonal mouse anti-human type I collagen as the primary antibody and horseradish peroxidase conjugated goat anti-mouse antibody as the secondary antibody. Collagen was quantitated by reading absorbance at 450 nm on a multiwell spectrophotometer. The amount of collagen per well was calculated from a standard curve of varying concentrations of human type I collagen.

As shown in FIG. 6, Chondroitinase B inhibited collagen secretion and incorporation into the extracellular matrix. The amount of collagen in the matrix of fibroblasts treated with 1 and 10 IU/ml of Chondroitinase B was significantly less than that of untreated cells. This effect was more pronounced with cells for which collagen synthesis had been stimulated with TGFβ.

Example 6

Inhibition of Fibroblast Proliferation in Mouse Skin Organ Cultures

Skin from Flaky skin mice (fsn/fsn) was used in these experiments. Flaky skin mice are a spontaneous mutant strain which develop skin lesions very similar to those seen in human psoriasis. (Sunderberg, et al. (1997) Pathobiology 65:271–286). The skin of these mice is noticeably thickened and scaly by 7 weeks of age. Histological examination shows extensive thickening of the epidermal layers, as well as the dermis. The increase in the dermis is due to the hyperproliferation of fibroblasts and an increase in collagen synthesis by these cells. Any pharmacological agent which decreases dermal thickness may have utility in treating diseases such as psoriasis and scleroderma.

Flaky skin organ cultures were utilized to evaluate the effects of Chondroitinase B on fibroblast proliferation and dermal thickening. Cultures were initiated and maintained, as has been described previously for human skin cultures (Varani, et al. (1994) Amer. J. Pathol. 145:561–573). Skin was obtained from 7 to 9 week old mice. Skin was washed 2× in DMEM containing a 5× concentration of penicillin/ streptomycin to prevent contamination of cultures with bacteria. Under sterile conditions, skin was cut into two $mm^2$ sections, and one section was placed in each well of 96 well dishes, along with 0, 0.1, 1.0 or 10 IU/ml of Chondroitinase B in Keratinocyte Growth Medium (Clonetics) containing 1.5 mM calcium. These cultures were maintained for 8 days, with a change of medium on days 1, 4 and 6.

On day 0, 3 and 7, some cultures were pulsed with 1 μCi of $^3$H-thymidine and harvested 24 hours later (day 1, 4, and 8). Thymidine labeled sections were used to assess fibroblast proliferation, measured by the incorporation of thymidine. These cultures were harvested and quantitiated as follows: Medium was removed and skin sections washed 2× with ice cold PBS. Ice cold 50% trichloroacetic acid (TCA) was added and cultures incubated at room temperature for 30 mins. TCA was removed and sections washed 2× in ice cold deionized water, and 2× in ice cold 95% ethanol. Sections were dried at room temperature for 3 hours, then individually weighed to obtain mg/ skin section. Sections were placed in scintillation fluid and counted, to quantitate cpm of thymidine incorporated per section, and the cpm/ mg tissue calculated from the weight of each section. For each of four mice, a minimum of 12 sections per time point were used. For each mouse, cpm/mg tissue incorporated by untreated skin (medium alone) was control. The % inhibition in enzyme treated skin was calculated using the control value for each mouse.

Figure 7:
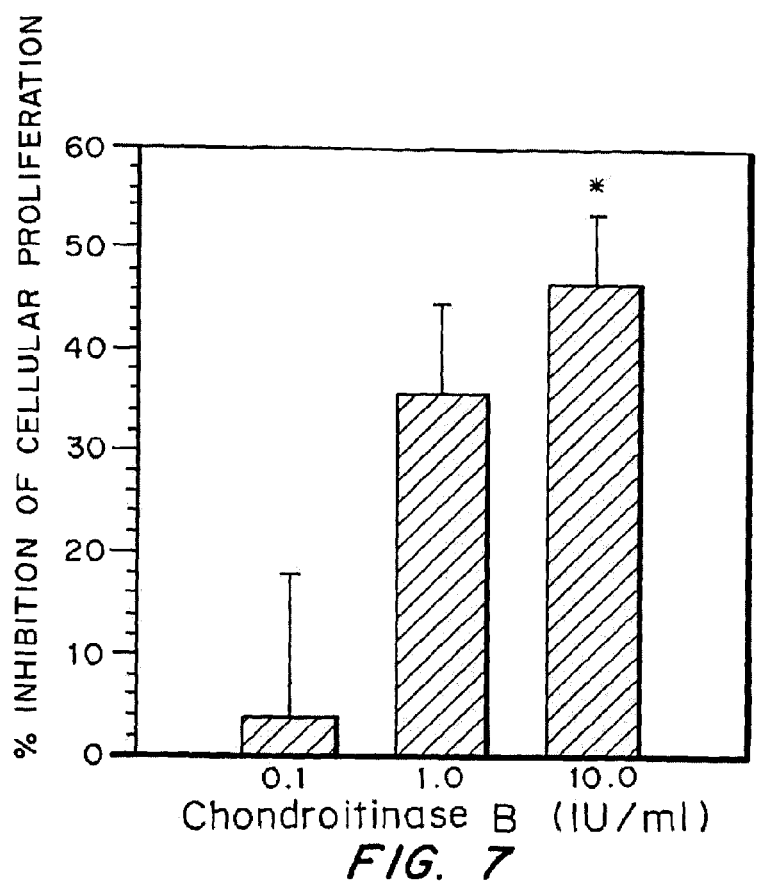
FIG. 7 is a graph of the inhibition of cell proliferation in mouse skin cultures treated for 8 days with 0.1 to 10 IU/ml of *Flavobacterium heparinum* derived chondroitinase B. Proliferation was assessed by the incorporation of 3H-thymidine into skin sections following a 24 hr exposure. Data are expressed as % inhibition when compared to controls (no enzyme). Each bar represents the mean±sem of 36 skin sections, taken from 3 mice. The * indicates inhibition was statistically significant with p<0.05.

There was no inhibition of fibroblast proliferation on day 1 or day 4. However, a decrease in proliferation was observed after skin sections were treated with 1 and 10 IU/ml of chondroitinase B for 8 days. As shown in FIG. 7, cell proliferation was inhibited by 35% and 48% respectively, in skin treated with 1.0 and 10 IU/ml of chondroitinase B. The effect in skin treated with 10 IU/ml was significant at a level of p=0.002, determined by ANOVA and Dunnet's group comparisons.

The effect of Chondroitinase B on skin was also evaluated in stained sections. On the day cultures were initiated (day 0) and days 4 and 8, untreated or enzyme-treated sections were fixed in 10% buffered formalin, embedded in paraffin, sectioned and stained with hematoxylin and eosin for histological examination. Assessment of sectioned skin was based on three sections/treatment/mouse/time point. For each section, a calibrated ocular micrometer was used to measure the thickness of the stratum corneum, the epidermis and the dermis. Three measurements of each layer were taken in different areas of the same section.

Figure 8:
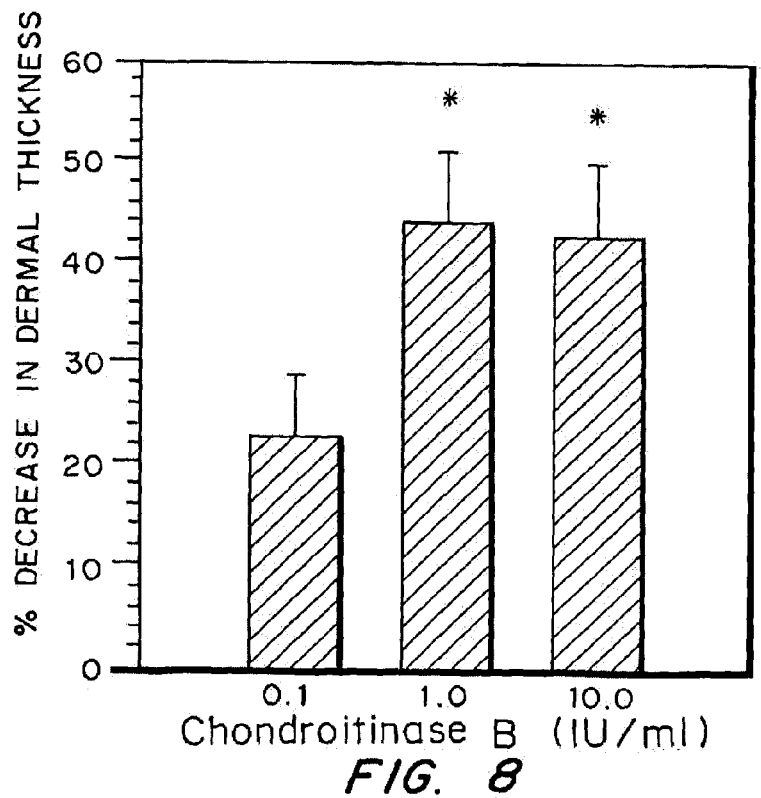
FIG. 8 is a graph of the decrease in dermal thickness in mouse skin cultures treated for 8 days with 0.1 to 10 IU/ml of *Flavobacterium heparinum* derived chondroitinase B. Data are expressed as % decrease compared to controls (no enzyme). Each bar represents the mean±sem of measurements taken from 18 skin sections, from 3 mice. The * indicates that inhibition (decrease in thickness) was statistically significant with p<0.05.
Figure 9A:
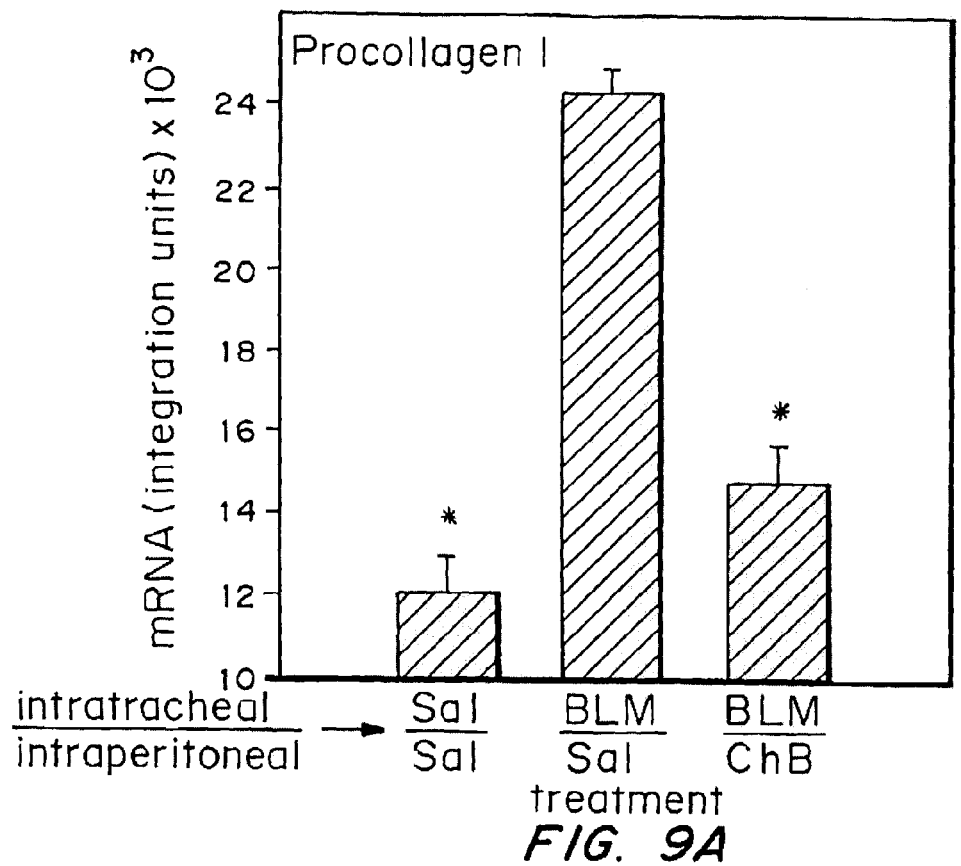
FIGS. 9a and 9b are graphs of the inhibition of the expression of mRNA for procollagen I (FIG. 9a) and TGFβ (FIG. 9b) in the lungs of mice treated with Chondroitinase B. Treatment groups indicate the route and substance injected into the trachea/ or peritoneal cavity respectively. ChB is 25 IU of enzyme per injection; BLM is one injection of 0.025 units of bleomycin sulfate; and SAL indicates the injection of equal volumes of saline. Data are expressed as integration units (×10$^3$) as determined by densitometry readings of Northern blot films. Each bar represents the mean±sem of 6 mice. The * indicates the decrease in mRNA expression was significantly less than that found in mice given BLM/SAL.
Figure 9B:
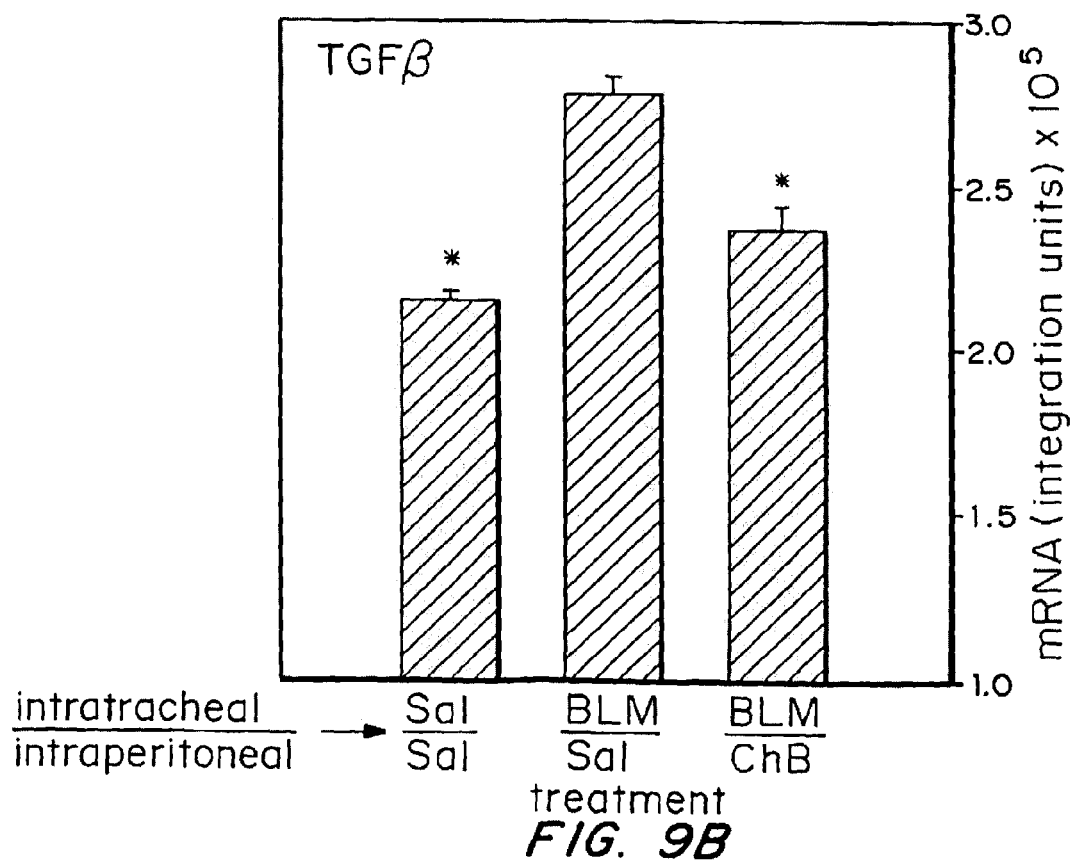

Based on the histological evaluation, there were no significant changes in the thickness of the stratum corneum or the epidermis. There was however a significant reduction in the thickness of the dermis, the skin layer containing dermal fibroblasts in cultures treated with chondroitinase B. As shown in FIG. 8, the thickness of the dermis in skin sections treated with 1.0 and 10 IU/ml of chondroitinase B was 36 and 40% less than that of controls. The reduced thickness of the dermal layer reflects a reduction in the number of fibroblasts, and is in agreement with the decreased cell proliferation, as measured by uptake of tritiated thymidine.

Example 7

Inhibition of the Expression of Procollagen and TGFβ in a Mouse Model of Pulmonary Fibrosis.

The effects of Chondroitinase B on the synthesis of type I collagen, and the collagen-promoting cytokine, TGFβ, were examined in a mouse model of pulmonary fibrosis. In this model, fibrosis is induced in the lungs of mice, by the intratracheal injection of the antineoplastic drug Blenoxane® (bleomycin sulfate). Bleomycin-induced fibrosis is very similar to human idiopathic pulmonary fibrosis, as documented by studies of the changes in morphology, biochemistry and mRNA in both mice and humans with this disease (Phan, S. H. Fibrotic mechanisms in lung disease. In: Immunology of Inflammation, edited by P. A. Ward, New York: Elsevier, 1983, pp121–162; Zhang et. al. (1994) Lab. Invest. 70: 192–202; Phan and Kunkel (1992) Exper. Lung Res. 18:29–43.)

Mice used in these experiments were CBA/J, which were 8 weeks old and approximately 25 g. Mice were divided into 3 treatment groups of 6 mice per group. Mice in each group were treated as follows:

| | GROUPS | | |
|---|---|---|---|
| DAY | 1 | 2 | 3 |
| 0 | i.t. saline | i.t. bleomycin 0.025 U in saline | i.t. bleomycin 0.025 U in saline |
| 3, 5, 7, 9, 11 | i.p. saline | i.p. saline | i.p. Chondroitinase B 20 IU in saline | i.t. - intratracheal administration;
i.p. = intraperitoneal injection

On Day 21, all mice were killed by lethal injection of sodium pentobarbital. Lungs were flushed with saline to remove blood, and mRNA extracted, and the expression of procollagen I, and TGFβ were assessed as described by Phan and Kunkel (1992; Exper. Lung Res. 18:29–43). The amount of mRNA contained in lungs of mice from the different treatment groups was quantified from densitometry readings from films following Northern blot analysis. The lungs of mice treated with bleomycin followed by Chondroitinase B, contained significantly less mRNA for both procollagen type I and for the collagen synthesis promoting cytokine, TGFβ. These results indicate that Chondroitinase B was effective in inhibiting the expression of mRNA for two key proteins which have shown to be greatly increased in fibrotic lungs.

We claim:

1. A method to modulate fibrous tissue formation comprising administering to an individual in need of treatment thereof an effective amount of a dermatan sulfate or chondroitin sulfate degrading enzyme.

2. The method of claim 1 wherein the enzyme is selected from the group consisting of bacterial dermatan or chondroitin sulfate degrading enzyme and is selected from the group consisting of chondroitinase AC from *Flavobacterium heparinum,* chondroitinase B from *Flavobacterium heparinum*, chondroitin sulfate degrading enzymes from *Bacteroides* species, chondroitin sulfate degrading enzymes from *Proteus vulgaris*, chondroitin sulfate degrading enzymes from *Micrococcus*, chondroitin sulfate degrading enzymes from *Vibrio* species, chondroitin sulfate degrading enzymes from *Arthrobacter aurescens*, arylsulfatase B, N-acetylgalactosamine-6-sulfatase and iduronate sulfatase from mammalian cells, these enzymes expressed from recombinant nucleotide sequences in bacteria and combinations thereof.

3. The method of claim 1 wherein the enzyme is a mammalian enzyme.

4. The method of claim 1 wherein the enzyme is a bacterial enzyme.

5. The method of claim 4 wherein the chondroitinase is chondroitinase B.

6. The method of claim 1 wherein the individual has a skin disorder.

7. The method of claim 6 wherein the skin disorder is scleroderma or psoriasis.

8. The method of claim 1 wherein the individual has keloid scarring or is at risk of keloid scarring, or has pulmonary fibrosis.

9. The method of claim 1 wherein the enzyme is administered systemically.

10. The method of claim 1 wherein the enzyme is administered topically or locally at or adjacent to a site in need of treatment.

11. The method of claim 1 wherein the enzyme is administered in a controlled and/or sustained release formulation.

* * * * *